United States Patent [19]

Fowler et al.

[11] 4,380,684

[45] Apr. 19, 1983

[54] LINEAR ALPHA OLEFIN PRODUCTION USING A TANK GROWTH REACTOR

[75] Inventors: Allan E. Fowler; Gordon E. White, both of Lake Jackson; Steve A. Sims, Angleton, all of Tex.

[73] Assignee: The Dow Chemical Company, Midland, Mich.

[21] Appl. No.: 369,458

[22] Filed: Apr. 19, 1982

Related U.S. Application Data

[63] Continuation-in-part of Ser. No. 269,119, Jun. 1, 1981, abandoned.

[51] Int. Cl.³ .......................... C07C 2/88; C07C 3/10
[52] U.S. Cl. .................................. 585/328; 585/522; 585/637
[58] Field of Search ...................... 585/328, 637, 522

[56] References Cited

U.S. PATENT DOCUMENTS

| | | | |
|---|---|---|---|
| 2,971,969 | 2/1961 | Lobo | 585/328 |
| 3,227,773 | 1/1966 | Roming | 585/328 |
| 3,457,320 | 7/1969 | Stapp et al. | 585/637 |
| 3,663,647 | 5/1972 | Lamier | 585/637 |

*Primary Examiner*—Curtis R. Davis
*Attorney, Agent, or Firm*—B. G. Colley

[57] ABSTRACT

A method for preparing $C_4$ to $C_{10}$ α-olefins employing trialkyl aluminum compounds, in a growth zone having a recirculation rate through an external heat transfer zone such that the contents of the zone are recirculated in a period of time sufficient to remove the heat of the reaction using added lower α-olefins at 100°–150° C., 200–2000 psig, and 5–90 minute contact time followed by displacement with lower α-olefins in a static mixer zone to free the growth α-olefins and regenerate the trialkyl aluminum compounds. The growth α-olefins are separated with all of the lower α-olefins recycled to the growth and displacement steps.

14 Claims, No Drawings

LINEAR ALPHA OLEFIN PRODUCTION USING A TANK GROWTH REACTOR

CROSS REFERENCE TO RELATED APPLICATIONS

This application is a continuation-in-part of Ser. No. 269,119, filed June 1, 1981 now abandoned.

BACKGROUND OF THE INVENTION

The production of alpha olefins having unbranched carbon skeletal configurations and terminal unsaturation has been practiced for 20 or more years. See for example, Chemical Engineering Progress 58:85-90 (June 1962) and U.S. Pat. No. 3,227,773, dated Jan. 4, 1966. With the advent of the triorganometallic compounds, viz, triethyl and tri-n-butyl aluminum, large scale commercial production has occurred. The primary and desired products are the $C_{12}$ to $C_{18}$ α-olefins for detergent use and the $C_{10+}$ for synthetic lubricants. The lower carbon atom compounds, viz, $C_6$ to $C_8$ have recently found utility in the polymer field and thus they are being recovered from the present day processes in increasing volume. In Ser. No. 179,348 filed Aug. 18, 1980, there is disclosed a process which provides for the production of increased amounts of $C_4$-$C_{10}$ alpha olefins.

The use of elongated coil growth reactors is well known from U.S. Pat. No. 2,971,969.

SUMMARY OF THE INVENTION

It is known to use coil reactors to perform the growth reaction step. However, these reactors require an olefin-:aluminum alkyl ratio of about 10 to 1 for best results. It has been found that by using a tank reactor with a relatively rapid external recirculation rate it is possible to use 2 to 6 moles of olefin per mole of aluminum alkyl and achieve yields of the desired hexene-1 and octene-1 after the displacement reaction which is as high as the system using coil reactors.

An added advantage of the present invention is the reduction in the amount of energy and capital equipment costs required by using the lower ratios of olefin. In fact, no excess olefin is required thereby eliminating costly recycle compression.

The growth promoting conditions used in the tank reactor are a temperature of 100° to 150° C. and preferably 115° to 125° C., a pressure range from 200 to 2000 pounds per square inch and preferably 300 to 1500 psig, and a liquid residence time of 15-60 minutes and preferably 30 to 40 minutes.

The growth reaction zone contents are recirculated through an external heat transfer zone at a recirculation rate such that the reaction zone contents are completely recirculated for a time sufficient to remove the heat of the reaction so as to maintain a substantially constant temperature. Preferably the recirculation time period is 0.1 to 30.0 minutes and 0.5 to 3.0 minutes is the most preferred time period.

A further aspect of the present invention is the use of a displacement zone containing a static mixer having 3 to 30 fixed elements which speeds up the displacement reaction.

BRIEF DESCRIPTION OF THE DRAWING

The invention is further illustrated by the FIGURE of the attached drawing.

In the drawing, 10 is a feed line supplying ethylene, propylene, or butene-1, and preferable ethylene which has been suitably purified to remove moisture and oxygen. Item 12 is a compressor wherein the lower olefin feed is brought up to a pressure of about 700 psig. The compressed olefin is then fed by line 14 to line 16 where it is combined with recycled catalyst from line 18 and circulated through the heat exchanger 17, the pump 19 and the recycle line 21 to the reactor inlet 22.

The pressurized tank or growth reactor 20 is provided with a gaseous outlet 23 for unreacted gases which circulate via line 25 through a heat exchanger 26 and line 28 to the displacement feed line 30. The combined liquid feed from line 30 and the gas feed from line 28 are thus combined to provide a feed to the displacement reactor 32. Reduction valves 24 and 27 are provided to maintain the high pressure in the reactor 20.

In the displacement reactor 32, liquid growth material is reacted with the displacement gases to generate growth α-olefins of $C_4$-$C_{20}$ and also recover the organo metallic catalyst. The reactor 32 is a conventional static mixer.

The contents of the displacement reactor 32 are fed by line 34 into the extraction column 36 wherein lower olefins or ethylene is stripped from the reaction mixture and is removed by outlet 42, and line 48. A recycle line 46, condenser 44 and a recycle inlet 40 is provided to remove the heavier gases and return them as liquid reflux. The line 48 carries the lower olefins to a compressor 50 where the gases are brought back up to the proper pressure for introduction by line 52 into the recycle line 28.

The bottoms from the tower 36 are removed by outlet 38 and introduced by line 39 into the tower 54 by inlet 53. In a manner similar to the tower 36, a higher olefin such as butene gas is stripped via the outlet 64, condenser 66 and inlet 62, with line 68 removing the butene gas to a takeoff valve 70 and transfer line 72. If desired, some or most of the butene can be withdrawn from valve 70 for use as an intermediate. The remaining butene is thus recycled by line 72 back to line 48 for reuse as a displacing gas.

The liquid bottoms in the butene tower 54 are recirculated via outlet 56, re-boiler 58, and inlet 60. The bottoms are fed by line 59 to inlet 74 of the vacuum tower 76 wherein the desired α-olefins ($C_6$-$C_{10}$) are separated from the catalyst mixture. The vacuum tower 76 is provided with a vacuum line 98 for the necessary reduction in pressure.

The bottoms from the vacuum tower 76 are drawn off by outlet 84 and circulated by pump 82 through a re-boiler 80 and back to the tower 76 by inlet 78.

A portion of the vacuum tower bottoms are recycled by line 86 back to the growth reactor 20. A reflux circuit for the vacuum tower 76 is provided by line 90, condenser 92 and inlet 94. A purge line 57 is provided to periodically remove $C_{12}$ and higher molecular weight material.

The vacuum tower overhead products are removed by outlet 88 and sent to a heat exchanger 96 and removed for further separation into the desired α-olefins.

DETAILED DESCRIPTION OF THE INVENTION

In accordance with the present invention, a lower olefin such as ethylene after being pressurized to a range from about 300 to 1000 psig is fed to a tank reactor maintained at a pressure of from about 200 to about 2000 psig and preferably from about 300 to about 1500 psig and a temperature of about 100° C. to about 150° C. and preferably from about 115° C. to about 125° C. wherein the olefin reacts with a trialkyl aluminum growth material, viz. triethyl aluminum or tributyl aluminum and preferably a mixture of the two, high in triethyl aluminum content. The reactor is of such size to enable the reactants to be in contact between about 5 and 90 minutes and preferably from about 30 to 40 minutes. Due to the exothermic reaction, the pressurized tank reactor is provided with an external heat transfer device so that the reaction zone contents are completely recirculated in a period of time from 0.25 to 5 minutes and preferably 0.5 to 3 minutes. Product withdrawn from the growth reactor is cooled to insure the growth products and any unreacted growth material remain in the liquid state yet the olefin or ethylene which has not reacted can be separated and returned to the growth reactor as recycle olefin.

The cooled liquid growth product and any unreacted growth material is then mixed with a displacement gas, such as α-olefin of 2–4 carbon atoms or preferably a mixture of ethylene and butene-1 in a static mixer displacement reactor of such size as to displace the material fed in under six seconds. The displacement gas is preheated to a temperature such that when mixed with the liquid feed stream at the displacement reactor, the temperature will be in the range from 200° C. to 350° C. and preferably in the range from 250° C. to 280° C. The reactor pressure is maintained at about 0–1000 psig and preferably in the range from 100 to 200 psig. The static mixer has 3 to 30 elements and preferably 6 to 12 elements so that a relatively short contact time in the range from 0.1 to 5 seconds, and is preferably in the range from 0.5 to 1.0 seconds, is achieved with complete mixing of the gas and liquid. The mol ratio of the displacement gas to each alkyl group of the trialkyl aluminum is in the range from 10:1 to 50:1 and preferably in the range 25:1 to 30:1.

The displacement product, the olefins and the tri lower alkyl aluminum product, is rapidly cooled to below about 150° C. and fed to the first stage of a separator 36 wherein the displacement gas and the olefins are removed and sent to a second stage separator 54 and the liquid product remaining is directed to a third stage separator 76. The gaseous products delivered to the second stage separator are further cooled and the displacement gases, removed, recompressed, heated, and recycled to the displacement reactor feed stream. The liquid bottoms product from the second separation is the desired olefins, in this case $C_4$ to $C_{10}$ α-olefins, which may be further separated in its constituent components. The third separator strips any remaining α-olefins from the tri lower alkyl aluminum growth material which olefins are combined with the α-olefins from the second separator and the latter, the lower alkyl aluminum compounds are recycled to the growth reactor.

Illustrative of the effectiveness of the tank reaction zone with recirculation, the conditions and results of thirteen typical examples are shown below wherein all percentages are in weight percent.

EXAMPLE 1

A 250 cc tank reactor was charged with the following materials:

| | |
|---|---|
| triethyl aluminum (TEA) | 17.07 gms |
| tri-n-butyl aluminum (TNBA) | 11.38 gms |
| tetradecane (n — $C_{14}$) | 28.45 gms |

This represents a 50% by weight aluminum alkyl feed stream.

The reactor had a bottom outlet connected to a recycle pump which pumped the reactor contents through a cooling coil back into the reactor.

A total of 31.8 grams of ethylene gas was charged at 700 psig. The reactor was brought to a 126° C. operating temperature via electric tape heaters. The pump was started and set to flow 50 cc/min. of liquid. This represents a 1½ minute reactor volume turnover.

The reaction was allowed to run for 30 minutes and then cooled down to room temperature. The aluminum alkyls were collected and a material balance was done. The aluminum alkyls, when slowly hydrolyzed, showed the following olefin yields:

| | |
|---|---|
| Butene-1 | 22.0% wt. |
| Hexene-1 | 58.7% wt. |
| Octene-1 | 16.6% wt. |
| Decene-1 | 2.6% wt. |
| $C_{12+}$ | 0.1% wt. |
| Total | 100.0% wt. |

EXAMPLE 2

Using the same reactor set up as Example No. 1, the following conditions were noted:

| Charge | |
|---|---|
| TEA | 11.4 gms |
| TNBA | 7.6 gms |
| n — $C_{14}$ | 76.0 gms |

The solution recycle rate was set at 50 cc/min. with the reactor operating at 700 psig and 113° C. A total of 35.3 grams of ethylene was charged to the reactor during the reactor operation.

After 30 minutes residence time, the following yields were noted:

| | |
|---|---|
| Butene-1 | 8.9% wt. |
| Hexene-1 | 61.3% wt. |
| Octene-1 | 23.7% wt. |
| Decene-1 | 5.8% wt. |
| $C_{12+}$ | 0.3% wt. |

EXAMPLE 3

Using the same reactor set up as Example No. 1, the following conditions were noted:

| Charge | |
|---|---|
| triethyl aluminum (TEA) | 28.5 grams |
| tri n-butyl aluminum (TNBA) | 19.0 grams |
| tetradecene (n — $C_{14}$) | 47.5 grams |

The solution recycle rate was set at 50 cc/min. This represents a 2.5 minute reactor volume turnover. A total 27.8 grams ethylene gas was charged with the reactor operating at 700 psig and 117° C. for 20 minutes residence time.

The following yields were noted:

| | |
|---|---|
| Butene-1 | 18.9% wt. |
| Hexene-1 | 66.9% wt. |
| Octene-1 | 13.0% wt. |
| Decene-1 | 1.2% wt. |
| $C_{12+}$ | 0.0% wt. |

EXAMPLE 4

Using the same reactor set up as Example No. 1, the following conditions were noted:

| Charge | |
|---|---|
| TEA | 16.9 grams |
| TNBA | 11.3 grams |
| n — $C_{14}$ | 28.2 grams |

The solution recycle rate was set at 75 cc/min. This represents a 1.0 minute reactor volume turnover. A total 32.2 grams ethylene gas was charged with the reactor operating at 700 psig and 120° C. for 30 minutes residence time.

The following yields were noted:

| | |
|---|---|
| Butene-1 | 19.6% wt. |
| Hexene-1 | 57.4% wt. |
| Octene-1 | 18.5% wt. |
| Decene-1 | 4.0% wt. |
| $C_{12+}$ | 0.5 wt. |

EXAMPLE 5

Using the same reactor set up as Example No. 1, the following conditions were noted:

| Charge | |
|---|---|
| TEA | 17.0 grams |
| TNBA | 11.3 grams |
| n — $C_{14}$ | 28.4 grams |

The solution recycle rate was set at 50 cc/min. This represents a 1.5 minute reactor volume turnover. A total 19.8 grams ethylene gas was charged with the reactor operating at 500 psig and 120° C. for 30 minutes residence time.

The following yields were noted:

| | |
|---|---|
| Butene-1 | 22.2% wt. |
| Hexene-1 | 57.6% wt. |
| Octene-1 | 16.2% wt. |
| Decene-1 | 3.5% wt. |
| $C_{12+}$ | 0.5% wt. |

EXAMPLE 6

Using the same reactor set up as Example No. 1, the following conditions were noted:

| Charge | |
|---|---|
| TEA | 16.8 grams |
| TNBA | 11.2 grams |
| n — $C_{14}$ | 28.0 grams |

The solution recycle rate was set at 50 cc/min. This represents a 1.5 minute reactor volume turnover. A total 29.8 grams ethylene gas was charged with the reactor operating at 700 psig and 110° C. for 30 minutes residence time.

The following yields were noted:

| | |
|---|---|
| Butene-1 | 22.23% wt. |
| Hexene-1 | 60.11% wt. |
| Octene-1 | 15.0% wt. |
| Decene-1 | 2.34% wt. |
| $C_{12+}$ | 0.32% wt. |

EXAMPLE 7

Using the same reactor set up as Example No. 1, the following conditions were noted:

| Charge | |
|---|---|
| TEA | 5.7 grams |
| TNBA | 3.8 grams |
| n — $C_{14}$ | 85.3 grams |

The solution recycle rate was set at 50 cc/min. This represents a 2.5 minute reactor volume turnover. A total 31.5 grams ethylene gas was charged with the reactor operating at 700 psig and 115° C. for 30 minutes residence time.

The following yields were noted:

| | |
|---|---|
| Butene-1 | 16.9% wt. |
| Hexene-1 | 60.8% wt. |
| Octene-1 | 17.6% wt. |
| Decene-1 | 3.9% wt. |
| $C_{12+}$ | 0.8% wt. |

EXAMPLE 8

Using the same reactor set up as Example No. 1, the following conditions were noted:

| Charge | |
|---|---|
| TEA | 11.4 grams |
| TNBA | 7.6 grams |
| n — $C_{14}$ | 76.0 grams |

The solution recycle rate was set at 50 cc/min. This represents a 2.5 minute reactor volume turnover. A total 35.3 grams ethylene gas was charged with the reactor operating at 700 psig and 113° C. for 30 minutes residence time.

The following yields were noted:

| | |
|---|---|
| Butene-1 | 8.8% wt. |
| Hexene-1 | 61.3% wt. |
| Octene-1 | 23.6% wt. |
| Decene-1 | 5.8% wt. |
| $C_{12+}$ | 0.5% wt. |

EXAMPLE 9

Using the same reactor set up as Example No. 1, the following conditions were noted:

| Charge | |
|---|---|
| TEA | 17.0 grams |
| TNBA | 11.3 grams |
| n — C$_{14}$ | 28.4 grams |

The solution recycle rate was set at 50 cc/min. This represents a 1.5 minute reactor volume turnover. A total 39.0 grams ethylene gas was charged with the reactor operating at 900 psig and 121° C. for 30 minutes residence time.
The following yields were noted:

| Butene-1 | 4.3% wt. |
|---|---|
| Hexene-1 | 56.2% wt. |
| Octene-1 | 26.7% wt. |
| Decene-1 | 9.8% wt. |
| C$_{12+}$ | 3.0% wt. |

EXAMPLE 10

Using the same reactor set up as Example No. 1, the following conditions were noted:

| Charge | |
|---|---|
| TEA | 22.68 grams |
| TNBA | 15.12 grams |
| n — C$_{14}$ | 37.80 grams |

The solution recycle rate was set at 67 cc/min. This represents a 1.5 minute reactor volume turnover. A total of 45.3 grams ethylene gas was charged with the reactor operating at 700 psig and 130° for 15 minutes residence time.
The following yields were noted:

| Butene-1 | 24.2% wt. |
|---|---|
| Hexene-1 | 55.3% wt. |
| Octene-1 | 16.4% wt. |
| Decene-1 | 3.5% wt. |
| C$_{12+}$ | 0.6% wt. |

EXAMPLE 11

Using the same reactor set up as Example No. 1, the following conditions were noted:

| Charge | |
|---|---|
| TEA | 22.68 grams |
| TNBA | 15.12 grams |
| n — C$_{14}$ | 37.80 grams |

The solution recycle rate was set at 67 cc/min. This represents a 1.5 minute reactor volume turnover. A total of 45.3 grams ethylene gas was charged with the reactor operating at 700 psig and 130° C. for 30 minutes residence time.
The following yields were noted:

| Butene-1 | 21.2% wt. |
|---|---|
| Hexene-1 | 53.2% wt. |
| Octene-1 | 19.8% wt. |
| Decene-1 | 5.0% wt. |
| C$_{12+}$ | 0.9% wt. |

EXAMPLE 12

Using the same reactor set up as Example No. 1, the following conditions were noted:

| Charge | |
|---|---|
| TEA | 17.04 grams |
| TNBA | 11.36 grams |
| n — C$_{14}$ | 28.40 grams |

The solution recycle rate was set at 50 cc/min. This represents a 1.5 minute reactor volume turnover. A total of 12.5 grams ethylene gas was charged with the reactor operating at 300 psig and 120° C. for 30 minutes residence time.
The following yields were noted:

| Butene-1 | 19.7% wt. |
|---|---|
| Hexene-1 | 75.4% wt. |
| Octene-1 | 4.9% wt. |
| Decene-1 | 0.0% wt. |
| C$_{12+}$ | 0.0% wt. |

EXAMPLE 13

Using the same reactor set up as Example No. 1, the following conditions were noted:

| Charge | |
|---|---|
| TEA | 17.07 grams |
| TNBA | 11.38 grams |
| n — C$_{14}$ | 28.45 grams |

The solution recycle rate was set at 50 cc/min. This represents a 1.5 minute reactor volume turnover. A total of 67.2 grams ethylene gas was charged with the reactor operating at 1500 psig and 120° C. for 30 minutes residence time.
The following yields were noted:

| Butene-1 | 13.3% wt. |
|---|---|
| Hexene-1 | 58.14% wt. |
| Octene-1 | 22.43% wt. |
| Decene-1 | 5.4% wt. |
| C$_{12+}$ | 0.73% wt. |

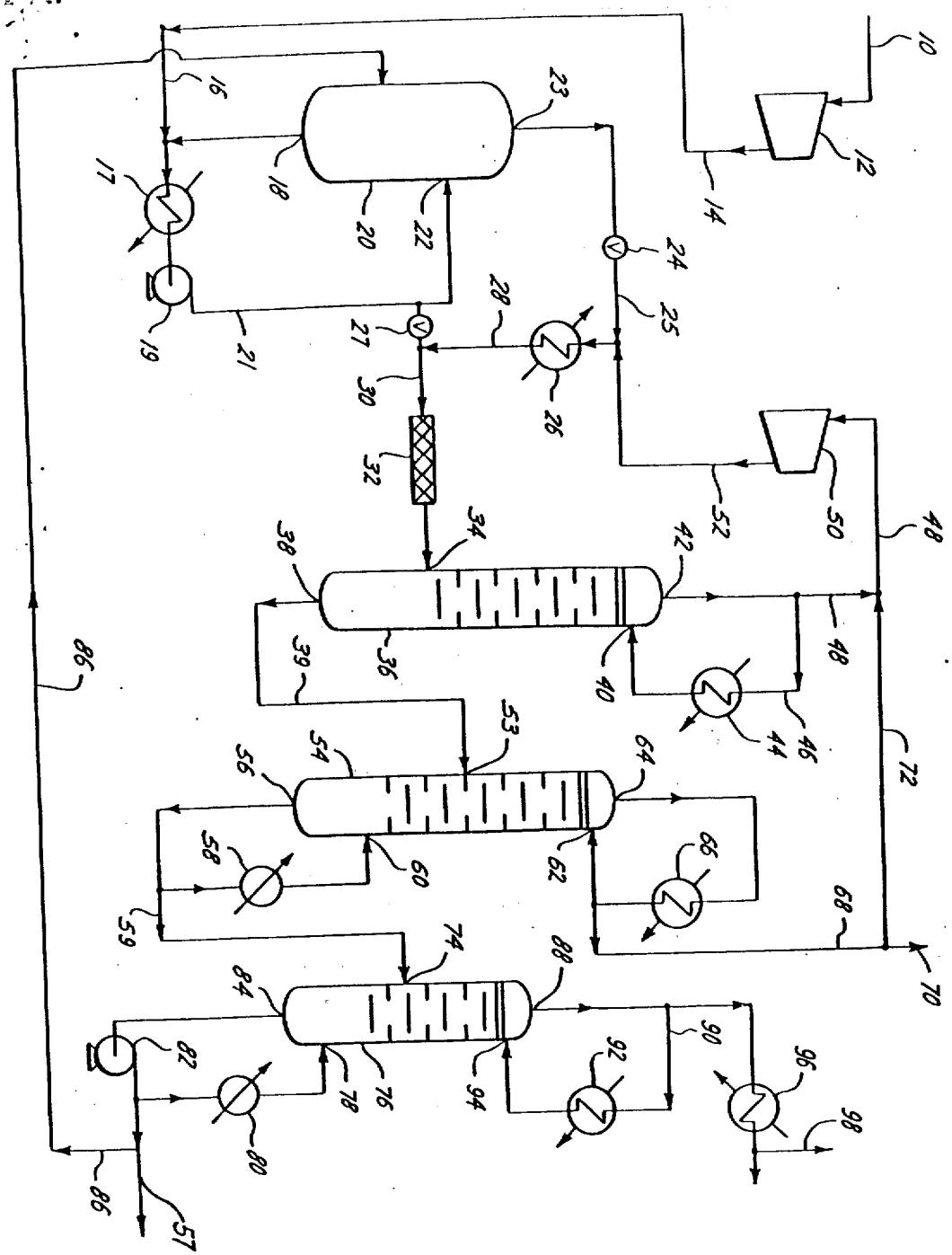

We claim:
1. In a process for making C$_4$–C$_{10}$ α-olefins wherein an α-olefin having 2–4 carbon atoms or mixtures thereof and low molecular weight trialkyl aluminum are reacted in a growth reaction zone under growth promoting conditions to provide higher molecular weight trialkyl aluminum and reacting an α-olefin having 2–4 carbon atoms or mixtures thereof with said higher trialkyl aluminum in a displacement reactor zone under displacement conditions to provide a mixture of C$_4$–C$_{10}$ α-olefins, the improvement which comprises providing a growth reaction zone by reacting 2 to 6 moles of α-olefin per mole of trialkyl aluminum in a tank reaction zone and having a recirculation rate through an external heat transfer zone such that the reaction zone contents are completely recirculated in a period of time sufficient to remove the heat of said reaction zone so as to maintain a substantially constant temperature therein.

2. The process as set forth in claim 1 wherein the recirculation time is 0.1 to 30.0 minutes.

3. The process as set forth in claim 1 wherein the recirculation time is 0.5 to 3.0 minutes.

4. The process as set forth in claim 1 wherein the growth promoting conditions are a temperature of 100° to 140° C., a pressure of 200 to 2000 psig, and a liquid residence time from 15 to 45 minutes.

5. The process as set forth in claim 1 wherein the growth promoting conditions are a temperature of 115° to 125° C., a pressure of 300 to 1500 psig, and a liquid residence time from 30 to 40 minutes.

6. A process for making $C_4$-$C_{10}$ α-olefins which comprises (A) reacting 2 to 6 moles of an α-olefin having 2-4 carbon atoms or mixtures thereof per mol of trialkyl aluminum in a tank reaction zone under a pressure of 200-2000 psig and a temperature in the range from 100° C. to 150° C. wherein said zone has a recirculation rate through an external heat transfer zone such that the contents thereof are recirculated in a period of time sufficient to remove the heat of said reaction zone so as to maintain a substantially constant temperature therein and to provide a growth product comprising higher trialkyl aluminum, (B) reacting an α-olefin having 2-4 carbon atoms, or mixtures thereof with said growth product in a displacement zone having a temperature in the range from 200° C. to 350° C., a pressure in the range from 0 to 1000 psig and a contact time in the range from 0.1 to 5 seconds, and (C) recovering the $C_4$-$C_{10}$ α-olefins.

7. The process as set forth in claim 6 wherein said displacement zone comprises a static mixer zone.

8. The process as set forth in claim 7 wherein said static mixer zone has 3 to 30 fixed elements.

9. The process as set forth in claim 6 wherein the recirculation time is 0.1 to 30.0 minutes.

10. The process as set forth in claim 6 wherein the recirculation time is 0.5 to 3.0 minutes.

11. A process for making $C_4$-$C_{10}$ α-olefins which comprises (A) reacting 2 to 6 moles of ethylene per mol of trialkyl aluminum in a tank reaction zone under a pressure of 200-2000 psig and a temperature in the range from 100° C. to 150° C. wherein said zone has a recirculation rate through an external heat transfer zone such that the contents thereof are recirculated in a period of time from 0.5 to 3 minutes to provide a growth product comprising higher trialkyl aluminum, (B) reacting ethylene or butene-1 or mixtures thereof with said growth product in a displacement zone having a temperature in the range from 200° C. to 350° C., a pressure in the range from 0 to 1000 psig and a contact time in the range from 0.1 to 5 seconds, and (C) recovering the $C_4$-$C_{10}$ α-olefins.

12. The process as set forth in claim 11 wherein said displacement zone comprises a static mixer zone.

13. The process as set forth in claim 12 wherein said static mixer zone has 3 to 30 fixed elements.

14. The process as set forth in claim 11 wherein the tank reaction zone is under a pressure of 300 to 1500 psig and has a temperature in the range from 115° to 125° C. and the displacement zone is under a pressure of 100 to 200 psig and has a temperature in the range from 250° to 280° C.

* * * * *

UNITED STATES PATENT AND TRADEMARK OFFICE
CERTIFICATE OF CORRECTION

PATENT NO. : 4,380,684

DATED : April 19, 1983

INVENTOR(S) : Allan E. Fowler, et al

It is certified that error appears in the above-identified patent and that said Letters Patent is hereby corrected as shown below:

On the title page, "no Drawing" should read
-- 1 Drawing --.

The single sheet of drawing should be added as shown on the attached sheet.

Signed and Sealed this

Twenty-third Day of April 1985

[SEAL]

Attest:

DONALD J. QUIGG

Attesting Officer   Acting Commissioner of Patents and Trademarks